(12) United States Patent
Nazarenko et al.

(10) Patent No.: US 10,494,676 B2
(45) Date of Patent: Dec. 3, 2019

(54) PROCESS FOR THE DIAGNOSIS OF CANCER BY USING EXOSOMES

(71) Applicants: Albert-Ludwigs-Universitaet Freiburg, Freiburg (DE); Karlsruher Institut für Technologie, Karlsruhe (DE)

(72) Inventors: Irina Nazarenko, Teningen Nimburg (DE); Andrew Cato, Eggenstein-Leopoldshafen (DE); Antje Neeb, Steinmauern (DE); Stefanie Bormann, Cologne (DE); Martin Schoenthaler, Freiburg (DE); Arkadiusz Miernik, Freiburg (DE); Malte Kroenig, Freiburg (DE); Konrad Wilhelm, Freiburg (DE); Benjamin Haenselmann, Freiburg im Breisgau (DE); Simon Hefele, Freiburg (DE)

(73) Assignees: Albert-Ludwigs-Universitaet Freiburg, Freiburg (DE); Karlsruher Institut Für Technologie, Karlsruhe (DE)

( * ) Notice: Subject to any disclaimer, the term of this patent is extended or adjusted under 35 U.S.C. 154(b) by 309 days.

(21) Appl. No.: 15/101,237

(22) PCT Filed: Dec. 1, 2014

(86) PCT No.: PCT/EP2014/076044
§ 371 (c)(1),
(2) Date: Jun. 2, 2016

(87) PCT Pub. No.: WO2015/082372
PCT Pub. Date: Jun. 11, 2015

(65) Prior Publication Data
US 2016/0298200 A1  Oct. 13, 2016

(30) Foreign Application Priority Data
Dec. 2, 2013  (EP) .................................. 13195330

(51) Int. Cl.
*C12Q 1/68* (2018.01)
*C12Q 1/6886* (2018.01)
*C12Q 1/6804* (2018.01)
*C12Q 1/6844* (2018.01)

(52) U.S. Cl.
CPC ......... *C12Q 1/6886* (2013.01); *C12Q 1/6804* (2013.01); *C12Q 1/6844* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS 6,171,816 B1 * 1/2001 Yu ..................... C07K 14/475
                                                          435/252.3
2011/0195426 A1 * 8/2011 Russo ............... C12N 15/1017
                                                          435/6.17

FOREIGN PATENT DOCUMENTS

WO   WO 2004/031239 A2   4/2004
WO   WO 2012/115885 A1   8/2012
WO   WO 2013/090620 A1   6/2013
WO   WO 2013/134786 A2   9/2013

OTHER PUBLICATIONS

Kani, K. et al. Anterior gradient 2 (AGR2): blood-based biomarker elevated in matastatic prostate cancer associated with the neuroendocrine phenotype (The Prostate, vol. 73, p. 306-315, 2013, published online Aug. 2012.*
Lowe er al. A computer program for selection of oligonucleotide primers for polymerase chain reactions. Nucleic Acids Res., Vo. 18 (7), p. 1757-1761, 1990.*
Nilsson, J. et al. Prostate cancer-derived urine exosomes: a novel approach to biomarkers for prostate cancer. British Journal of Cancer, vol. 100, p. 1603-1607, 2009.*
Bu, H. et al. The anterior gradient 2 (AGR2) gene is overexpressed in prostate cancer and may be useful as a urine sediment marker for prostate cancer detection. The Prostate, Vo. 71, p. 575-587, 2011.*
Huajie, Bu et al., "The Anterior Gradient 2 (AGR2) Gene is Overexpressed in Prostate Cancer and may be Useful as a Urine Sediment Marker for Prostate Cancer Detection", *The Prostate*, vol. 71. No. 6, pp. 575-587 (Oct. 2010).
Kani, Kian et al., "Anterior Gradient 2 (AGR2): Blood-Based Biomarker Elevated in Metastatic Prostate Cancer Associated with the Neuroendocrine Phenotype", *The Prostate*, vol. 73. No. 3, pp. 306-315 (Aug. 2012).

(Continued)

*Primary Examiner* — Suryaprabha Chunduru
(74) *Attorney, Agent, or Firm* — Chalin A. Smith; Smith Patent, LLC

(57) ABSTRACT

The present invention relates to an in vitro process for the diagnosis of prostate cancer and other tumor types in exosomes obtained from a body fluid which comprises
a) concentrating the exosomes and other extracellular vesicles from a body fluid of a patient,
b) extraction of total RNA from the exosomes obtained in step a),
c) conversion of the RNA obtained in step b) to cDNA,
d) amplification of the cDNA obtained in step c) with a polymerase chain reaction whereby primers derived from the AGR2 nucleotide sequence or the complement thereof are used, and
e) determining whether in the amplification product variants of the AGR2 gene can be identified.

13 Claims, 15 Drawing Sheets
Specification includes a Sequence Listing.

(56) References Cited

OTHER PUBLICATIONS

Nilsson J. et al., "Prostate Cancer-Derived Urine Exosomes: A Novel Approach to Biomarkers for Prostate Cancer", British Journal of Cancer, vol. 100, No. 10, pp. 1603-1607 (May 2009).

Diederick, Duijvesz et al., "Exosomes as Biomarker Treasure Chests for Prostate Cancer", European Urology, vol. 59, No. 5, pp. 823-831 (Dec. 2010).

Brychtova, Veronika et al., "Anterior Gradient 2: A Novel Player in Tumor Cell Biology", Cancer Letters, vol. 304, No. 1, pp. 1-7 (Dec. 2010).

Vivekanandan, P. et al., Anterior Gradient-2 is Overexpressed by Fibrolamellar Carcinomas, Human Pathology, vol. 40, No. 3, pp. 293-299 (Mar. 2009).

Pizzi, Marco et al., "Anterior Gradient 2 Overexpression in Lung Adenocarcinoma", Applied Immunohistochemical & Molecular Morphology, vol. 20, No. 1, pp. 31-36 (Jan. 2012).

Neeb, Antje et al., "Splice Variant Transcripts of the Anterior Gradient 2 Gene as a Marker for Prostate Cancer", Oncotarget, vol. 5, No. 18., pp. 8681-8689 (Sep. 2014).

Ringsrud, Karen M., "Cells in the Urine Sediment", Laboratory Medicine, vol. 32, No. 3, pp. 153-155(Mar. 2001).

Karen M. Ringsrud, MT (ASCP), "Cells in the Urine Sediment", *Laboratory Medicine*, Mar. 2001, vol. 32, No. 3, pp. 153-155.

\* cited by examiner

| blood plasma EV | radius (nm) | StdDev (nm) | distribution by signal intensity (%) | distribution by mass (%) | distribution by number (%) |
|---|---|---|---|---|---|
| population 1 | 4.7 | 0.7 | 15 | 95 | 99.9 |
| population 2 | 23.6 | 3.2 | 43 | 4.6 | 0.09 |
| population 3 | 254.2 | 29.5 | 41 | 0.5 | 0.01 |

| urine EV | radius (nm) | StdDev (nm) | distribution by signal intensity (%) | distribution by mass (%) | distribution by number (%) |
|---|---|---|---|---|---|
| population 1 | 74 | 85.9 | 100 | 52.90 | 100 |

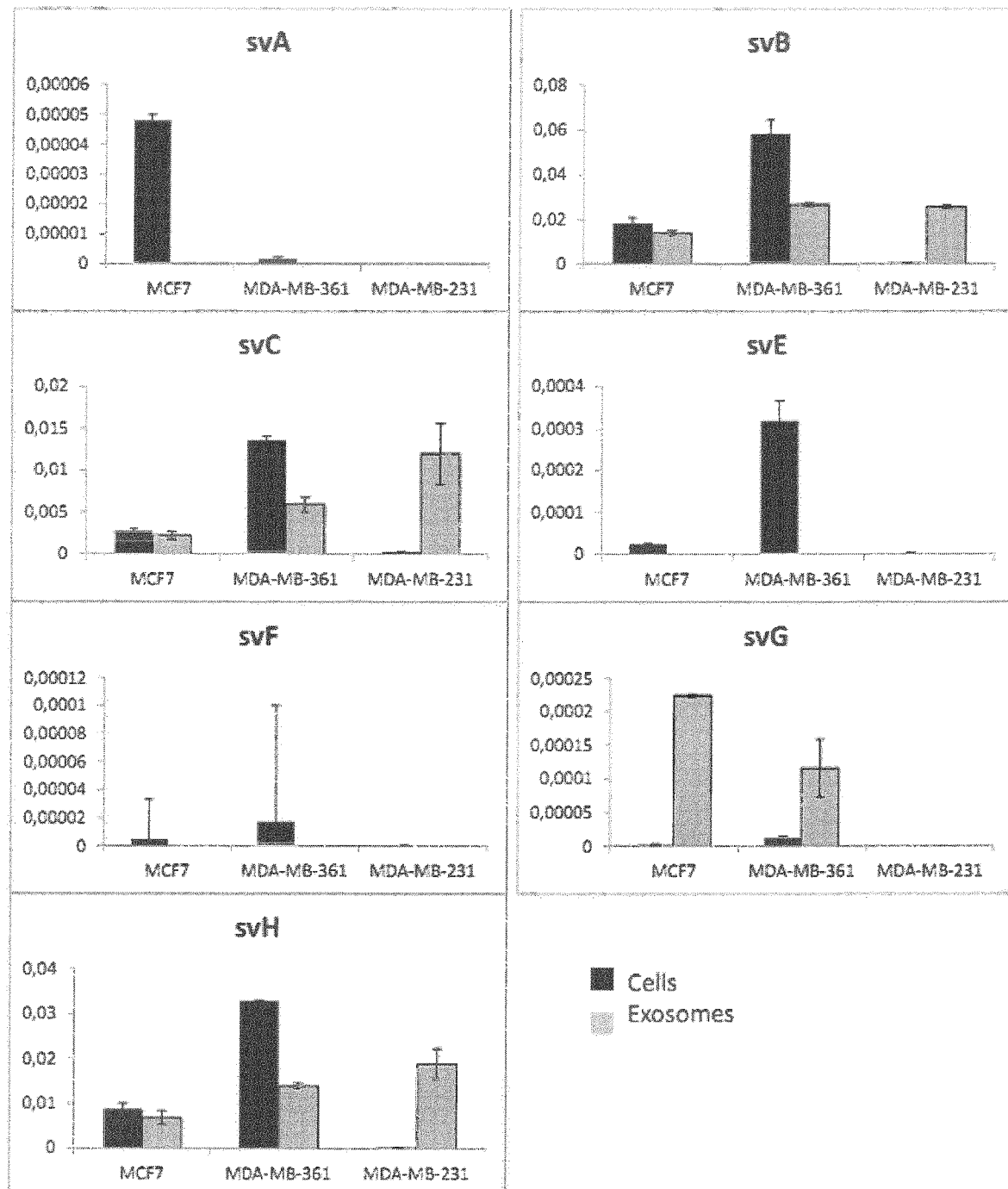
Fig. 6  Comparative analysis of *AGR2* SVs mRNA levels in breast cancer cells and in exosomes Fig. 7  AGR2 SVs mRNA levels in exosomes isolated from the urine of 4 patients with urothelial carcinoma
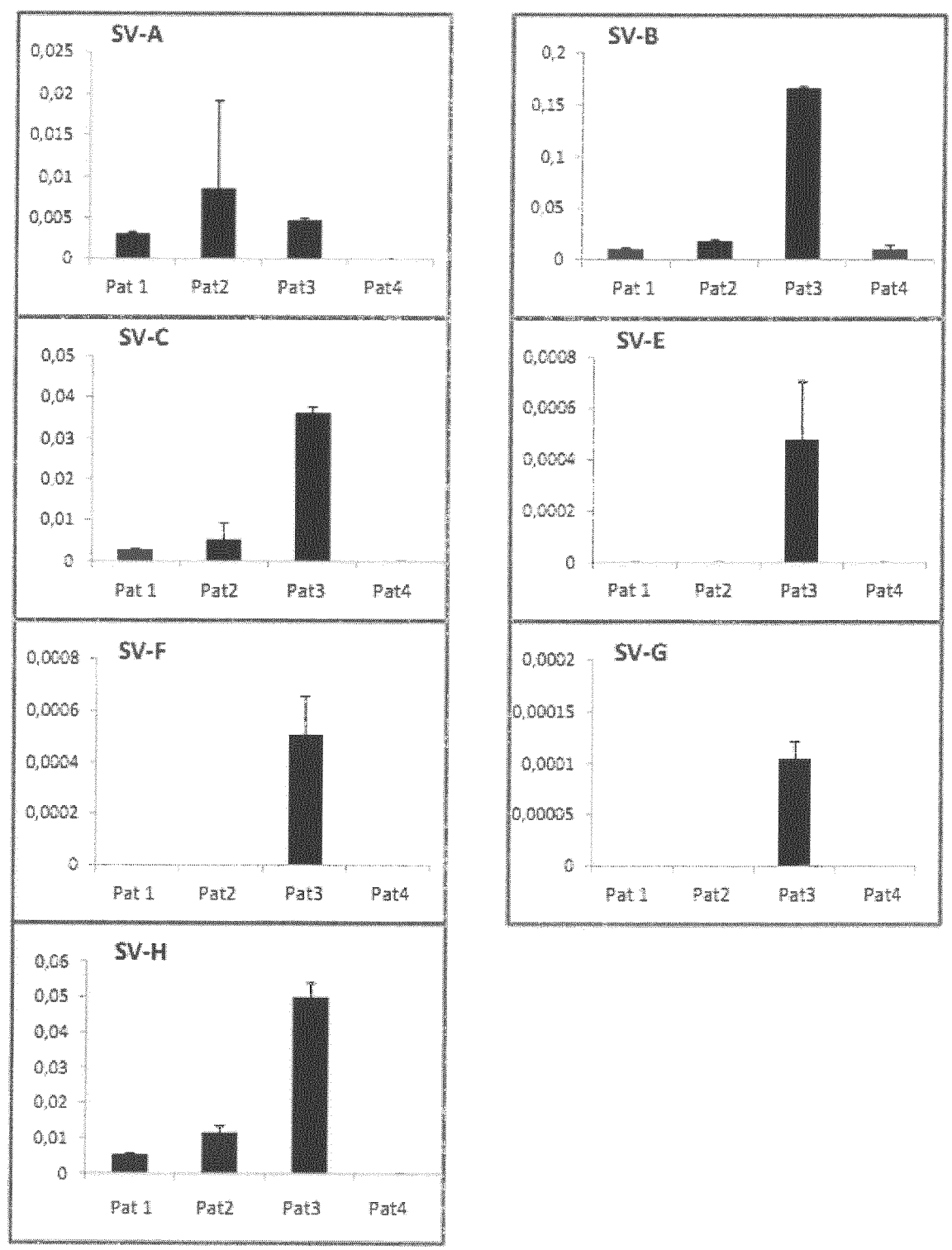

Fig. 8 *AGR2* SVs mRNA levels in exosomes isolated from the urine of 4 patients with renal cell carcinoma
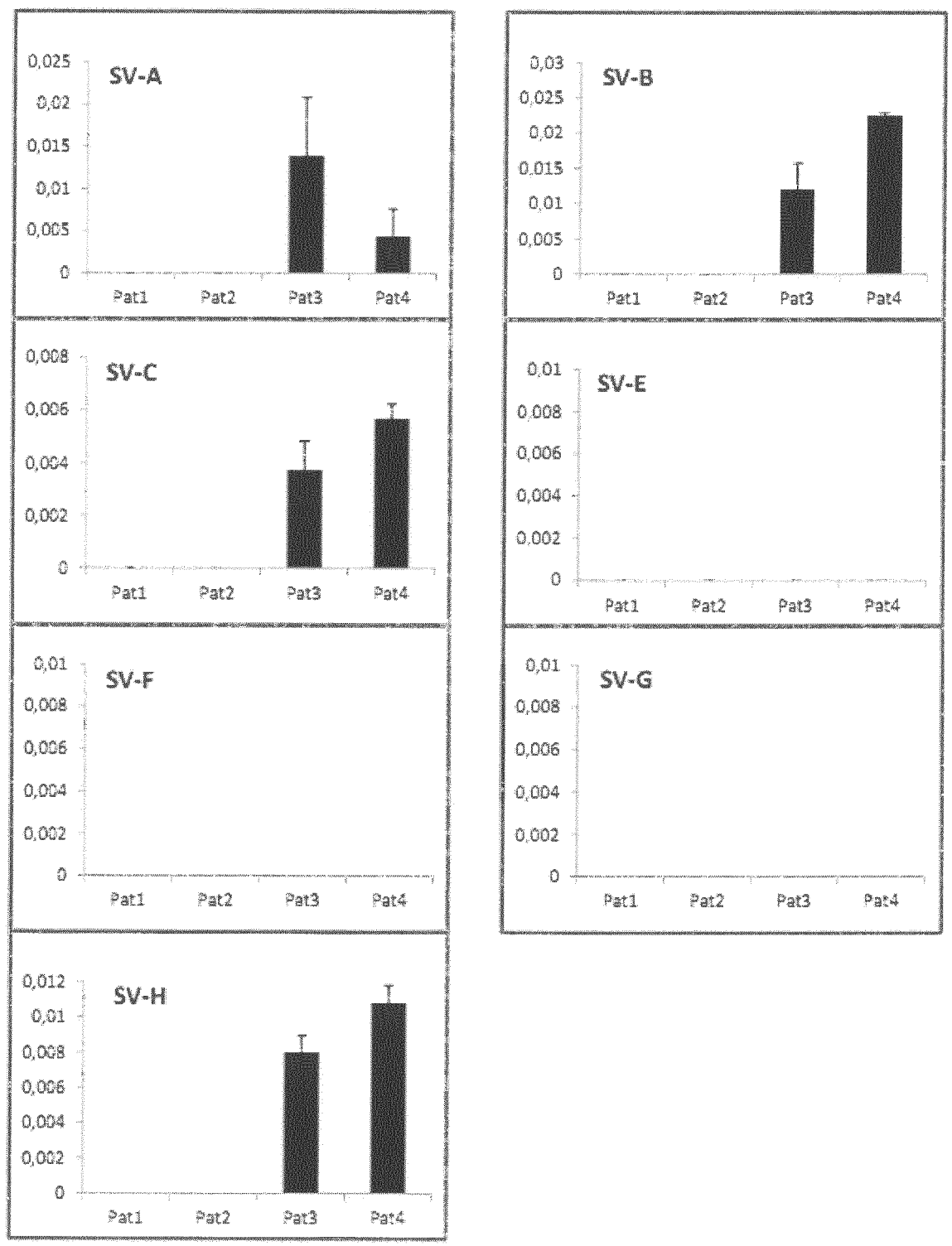

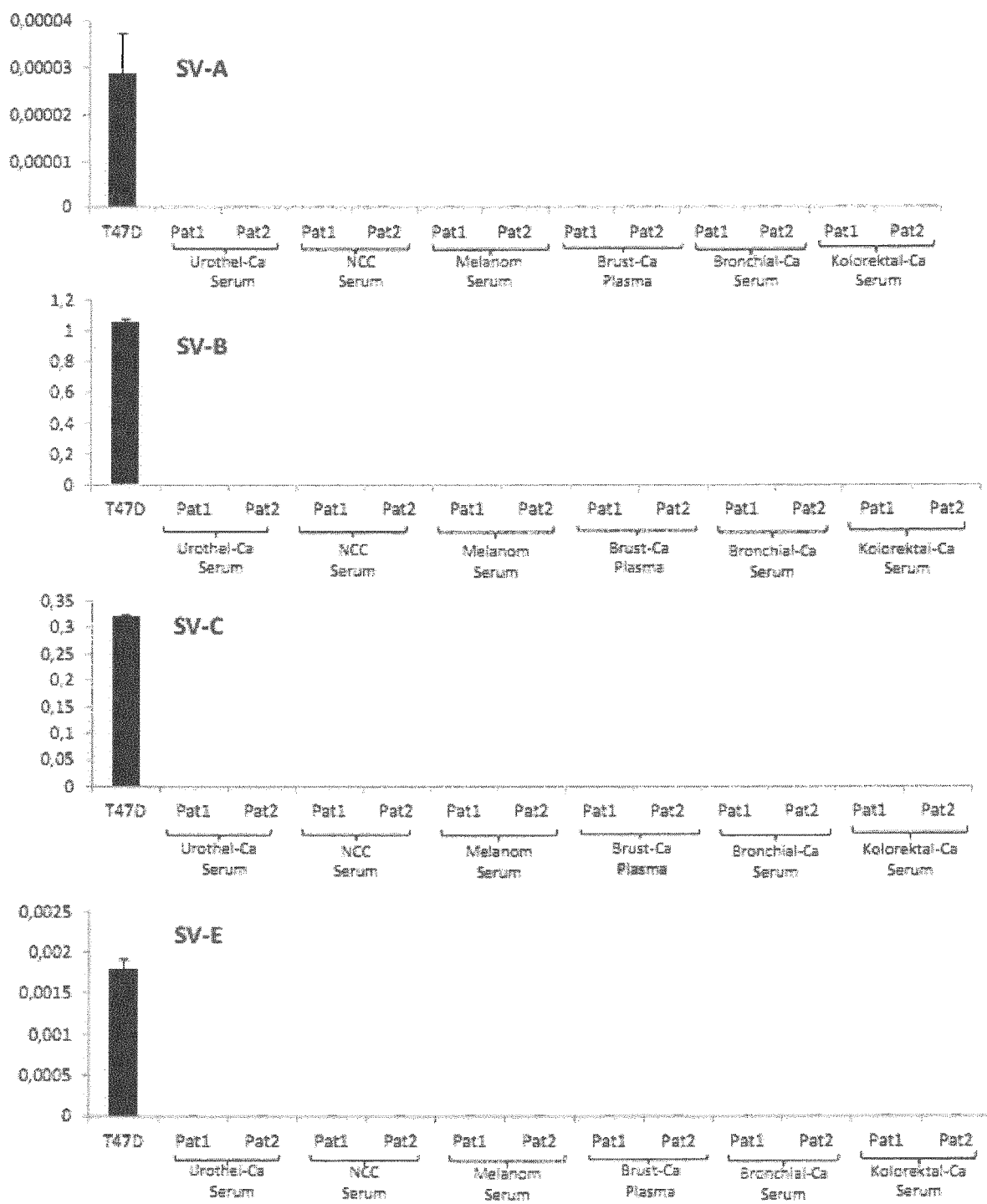
Fig. 9A  *AGR2* SVs mRNA levels in exosomes isolated from blood (serum or plasma) of patients with different tumor types

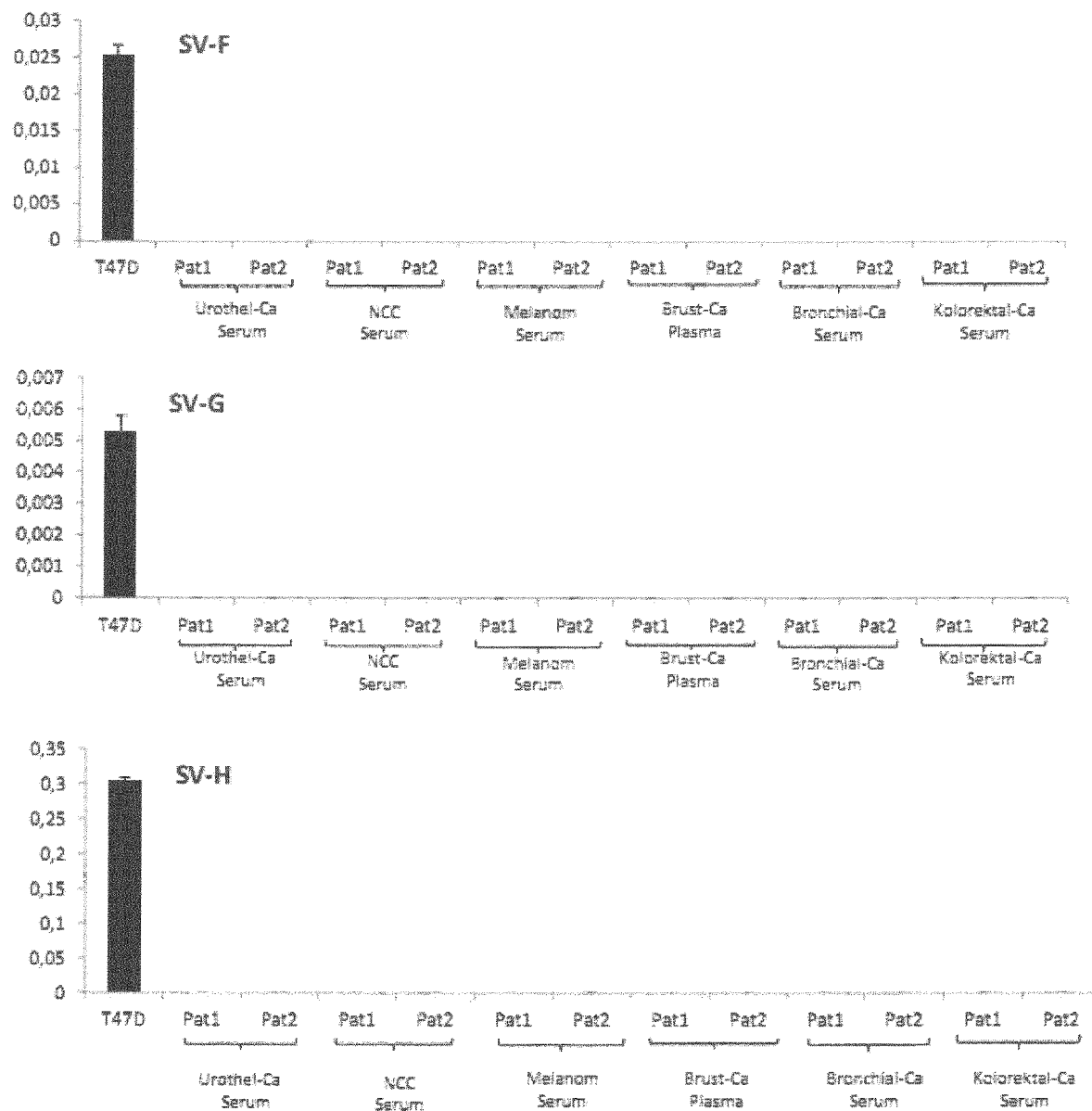
Fig. 9B  *AGR2* SVs mRNA levels in exosomes isolated from blood (serum or plasma) of patients with different tumor types

SEQUENCE LISTING

<160> NUMBER OF SEQ ID NOS: 15

<210> SEQ ID NO 1
<211> LENGTH: 1077
<212> TYPE: DNA
<213> ORGANISM: homo sapiens

<400> SEQUENCE: 1

```
accgcatcct agccgccgac tcacacaagg caggtgggtg aggaaatcca gagttgccat      60
ggagaaaatt ccagtgtcag cattcttgct ccttgtggcc ctctcctaca ctctggccag     120
agataccaca gtcaaacctg gagccaaaaa ggacacaaag gactctcgac ccaaactgcc     180
ccagaccctc tccagaggtt ggggtgacca actcatctgg actcagacat atgaagaagc     240
tctatataaa tccaagacaa gcaacaaacc cttgatgatt attcatcact tggatgagtg     300
cccacacagt caagctttaa agaaagtgtt tgctgaaaat aaagaaatcc agaaattggc     360
agagcagttt gtcctcctca atctggttta tgaaacaact gacaaacacc tttctcctga     420
tggccagtat gtccccagga ttatgtttgt tgacccatct ctgacagtta gagccgatat     480
cactggaaga tattcaaatc gtctctatgc ttacgaacct gcagatacag ctctgttgct     540
tgacaacatg aagaaagctc tcaagttgct gaagactgaa ttgtaaagaa aaaaaatctc     600
caagcccttc tgtctgtcag gccttgagac ttgaaaccag aagaagtgtg agaagactgg     660
ctagtgtgga agcatagtga acacactgat taggttatgg tttaatgtta caacaactat     720
tttttaagaa aaacatgttt tagaaatttg gtttcaagtg tacatgtgtg aaaacaatat     780
tgtatactac catagtgagc catgattttc taaaaaaaaa ataaatgttt tgggggtgtt     840
ctgttttctc caacttggtc tttcacagtg gttcgtttac caaataggat taaacacaca     900
caaaatgctc aaggaaggga caagacaaaa ccaaaactag ttcaaatgat gaagaccaaa     960
gaccaagtta tcatctcacc acaccacagg ttctcactag atgactgtaa gtagacacga    1020
gcttaatcaa cagaagtatc aagccatgtg ctttagcata aaaaaaaaaa aaaaaaa     1077
```

<210> SEQ ID NO 2
<211> LENGTH: 175
<212> TYPE: PRT
<213> ORGANISM: homo sapiens

<400> SEQUENCE: 2

```
Met Glu Lys Ile Pro Val Ser Ala Phe Leu Leu Leu Val Ala Leu Ser
1               5                   10                  15

Tyr Thr Leu Ala Arg Asp Thr Thr Val Lys Pro Gly Ala Lys Lys Asp
            20                  25                  30

Thr Lys Asp Ser Arg Pro Lys Leu Pro Gln Thr Leu Ser Arg Gly Trp
        35                  40                  45

Gly Asp Gln Leu Ile Trp Thr Gln Thr Tyr Glu Glu Ala Leu Tyr Lys
    50                  55                  60

Ser Lys Thr Ser Asn Lys Pro Leu Met Ile Ile His His Leu Asp Glu
```

```
                65                  70                  75                  80
Cys Pro His Ser Gln Ala Leu Lys Lys Val Phe Ala Glu Asn Lys Glu
                    85                  90                  95

Ile Gln Lys Leu Ala Glu Gln Phe Val Leu Leu Asn Leu Val Tyr Glu
                100                 105                 110

Thr Thr Asp Lys His Leu Ser Pro Asp Gly Gln Tyr Val Pro Arg Ile
            115                 120                 125

Met Phe Val Asp Pro Ser Leu Thr Val Arg Ala Asp Ile Thr Gly Arg
        130                 135                 140

Tyr Ser Asn Arg Leu Tyr Ala Tyr Glu Pro Ala Asp Thr Ala Leu Leu
145                 150                 155                 160

Leu Asp Asn Met Lys Lys Ala Leu Lys Leu Leu Lys Thr Glu Leu
                    165                 170                 175

<210> SEQ ID NO 3
<211> LENGTH: 21
<212> TYPE: DNA
<213> ORGANISM: artificial sequence
<220> FEATURE:
<223> OTHER INFORMATION: SV C: Forward

<400> SEQUENCE: 3
cacaaggcag agttgccatg g                                              21

<210> SEQ ID NO 4
<211> LENGTH: 20
<212> TYPE: DNA
<213> ORGANISM: artificial sequence
<220> FEATURE:
<223> OTHER INFORMATION: SV E: Forward

<400> SEQUENCE: 4
atctggtcac ccatctctga                                                20

<210> SEQ ID NO 5
<211> LENGTH: 21
<212> TYPE: DNA
<213> ORGANISM: artificial sequence
<220> FEATURE:
<223> OTHER INFORMATION: SV F: Forward

<400> SEQUENCE: 5
ggaaatccag acccatctct g                                              21

<210> SEQ ID NO 6
<211> LENGTH: 18
<212> TYPE: DNA
<213> ORGANISM: artificial sequence
<220> FEATURE:
<223> OTHER INFORMATION: SV G: Forward

<400> SEQUENCE: 6
aaggcaggta cagctctg                                                  18

<210> SEQ ID NO 7
<211> LENGTH: 22
<212> TYPE: DNA
<213> ORGANISM: artificial sequence
<220> FEATURE:
<223> OTHER INFORMATION: Reverse SV C, E, F G

<400> SEQUENCE: 7
tccacactag ccagtcttct ca                                             22
```

<210> SEQ ID NO 8
<211> LENGTH: 24
<212> TYPE: DNA
<213> ORGANISM: artificial sequence
<220> FEATURE:
<223> OTHER INFORMATION: SV H Forward:

<400> SEQUENCE: 8
atggagaaaa ttccagtgtc agca                                    24

<210> SEQ ID NO 9
<211> LENGTH: 24
<212> TYPE: DNA
<213> ORGANISM: artificial sequence
<220> FEATURE:
<223> OTHER INFORMATION: SV H Reverse

<400> SEQUENCE: 9
agacatatga agaacctctc aagt                                    24

<210> SEQ ID NO 10
<211> LENGTH: 20
<212> TYPE: DNA
<213> ORGANISM: artificial sequence
<220> FEATURE:
<223> OTHER INFORMATION: GR2LtForward

<400> SEQUENCE: 10
gccaacagac aacccaaagt                                         20

<210> SEQ ID NO 11
<211> LENGTH: 20
<212> TYPE: DNA
<213> ORGANISM: artificial sequence
<220> FEATURE:
<223> OTHER INFORMATION: AGR2LtReverse

<400> SEQUENCE: 11
gcaagaatgc tgacactgga                                         20

<210> SEQ ID NO 12
<211> LENGTH: 19
<212> TYPE: DNA
<213> ORGANISM: artificial sequence
<220> FEATURE:
<223> OTHER INFORMATION: AGR2St forward  short transkript

<400> SEQUENCE: 12
cgactcacac aaggcaggt                                          19

<210> SEQ ID NO 13
<211> LENGTH: 20
<212> TYPE: DNA
<213> ORGANISM: artificial sequence
<220> FEATURE:
<223> OTHER INFORMATION: AGR2St reverse short transcript

<400> SEQUENCE: 13
gcaagaatgc tgacactgga                                         20

<210> SEQ ID NO 14
<211> LENGTH: 22
<212> TYPE: DNA
<213> ORGANISM: artificial sequence
<220> FEATURE:

-continued

```
<223> OTHER INFORMATION: PSA Foward

<400> SEQUENCE: 14
accagaggag ttcttgaccc ca                                        22

<210> SEQ ID NO 15
<211> LENGTH: 20
<212> TYPE: DNA
<213> ORGANISM: artificial sequence
<220> FEATURE:
<223> OTHER INFORMATION: PSA Reverse

<400> SEQUENCE: 15
ccccagaatc acccgagcag                                           20
```

PROCESS FOR THE DIAGNOSIS OF CANCER BY USING EXOSOMES

PRIORITY

This application corresponds to the U.S. national phase of International Application No. PCT/EP2013/076044, filed Dec. 1, 2014, which, in turn, claims priority to European Patent Application No. 13.195330.9 filed Dec. 2, 2013, the contents of which are incorporated by reference herein in their entirety.

SEQUENCE LISTING

The instant application contains a Sequence Listing that has been submitted in ASCII format via EFS-Web and is hereby incorporated by reference in its entirety. Said ASCII copy, created on Jun. 2, 2016, is named LNK_176US_SequenceListing_ST25.txt and is 5,699 bytes in size.

BACKGROUND OF THE INVENTION

Prostate cancer has become a major public health problem. In many developed countries it is not only the most commonly diagnosed malignancy but it is the second leading cause of cancer related deaths in males.

Since its discovery more than 20 years ago, prostate specific antigen (PSA) has been the most valuable tool in the detection, staging and monitoring of prostate cancer. Although widely accepted as a prostate tumour marker, PSA is known to be prostate tissue—but not prostate cancer-specific. PSA levels have been reported to increase in men with benign prostatic hyperplasia (BPH) and prostatitis. This substantial overlap in serum PSA values between men with non-malignant prostatic diseases and prostate cancer is the limitation of PSA as a prostate tumour marker. Moreover, a single reading of PSA cannot be used to differentiate the aggressive tumours from the indolent ones. Thus, (non-invasive) molecular tests that can accurately identify those men who have early stage, clinically localized prostate cancer, and who would gain prolonged survival and quality of life from early radical intervention are urgently needed.

Looking for new diagnostic, prognostic markers as well as understanding the molecular mechanisms underlying the disease progress and progression process and identify new treatment targets is the main focus for current prostate cancer research. For the identification of new candidate markers for prostate cancer it is necessary to study expression patterns in malignant as well as non-malignant prostate tissues. One of the genes identified to be overexpressed in prostate cancer is the anterior gradient 2 (AGR2) gene (Bu et al., The Prostate (2011), 575-587). The authors describe long and short transcripts of AGR2 (anterior gradient-2) being up-regulated in prostate cancer cells and tissues. RNAs were isolated from microdissected frozen prostate tissue samples obtained from radical prostatectomy specimens. Total RNA was amplified, reverse transcribed into cDNA and subjected to quantitative real-time PGR. Two transcript variants of the AGR2 gene were detected. Expression of short AGR2 transcript was up-regulated in tumors. Although AGR2 short transcript mRNA level showed slightly higher sensitivity and specificity as compared to the PSA serum level, no significant differences could be observed. Therefore, mRNA level of the AGR2 short transcript in tissue or in the urine sediment are considered as not applicable for a reliable detection of prostate carcinoma.

Nilsson et al., British Journal of Cancer (2009) 100, 1603-1607 analyze prostate cancer-derived urine exosomes as novel approach to biomarkers for prostate cancer. The authors describe the application of urine exosomes as a source for prostate cancer biomarkers. Thereby, mRNA levels of two known prostate cancer biomarkers designated as PCA-3 and TMPRSS2:ERG were tested in several patients. For the detection of corresponding mRNA a prostate massage was applied prior to urine harvesting which is not applicable in routine daily praxis. The article does, however, not provide data about the status of the tumor markers in tumor tissues. Consequently it is not possible to evaluate the diagnostic and/or prognostic values of the suggested biomarkers. A potential enrichment of the two biomarkers PCA-3 and TMPRSS2:ERG in urine exosomes seems to be at least questionable. Since the article shows only slightly higher specificity and sensitivity for prostate cancer detection as compared to the frequently used PSA serum level the test described in this article does not seem promising for the implementation into daily clinical routine.

SUMMARY OF THE INVENTION

The present invention as defined in more detail in the claims shows significantly better sensitivity and specificity of AGR2 splice variants as compared to the serum PSA. This makes the AGR2 splice variants as described herein highly specific and promising diagnostic markers.

AGR2 was first described in *Xenopus laevis* embryos where it induces the formation of the forebrain and the cement gland. In humans, it is predominantly found in mucus-secreting tissues or in endocrine cells. It is a member of the protein disulfide isomerase family of endoplasmic reticulum-resident proteins that has been implicated in the folding of proteins. It became of interest in cancer research, when it was found to be differential expressed in estrogen receptor (ER)-positive breast cancer cell lines. Since then, elevated AGR2 has been reported in subsets of breast, prostate, non-small cell lung, pancreatic, and hepatic adenocarcinomas. In some cases its increased expression has been shown to be of prognostic value. Furthermore elevated AGR2 RNA levels have been shown to correlate with decreased efficacy of tamoxifen treatment. AGR2 transcript level is therefore postulated to serve as a potential predictive biomarker for selection of optical algorithm for adjuvant hormonal therapy in postmenopausal ER-positive breast cancer patients.

The AGR2 gene has been deposited at the Genebank and is available under accession number AF038451. The nucleotide sequence (SEQ ID NO:1) can be downloaded from the gene bank as well as the protein sequence (SEQ ID NO:2).

With the use of transcript-specific primers the expression of AGR2 transcript variants in microdissected prostate tissues was investigated. A real-time reverse transcription polymerase chain reaction (PGR) method to detect AGR2 in exosomes was established in order to test its potential as a predictive marker for prostate cancer and potentially in other tumors. AGR2 is highly expressed in prostate cancer especially in low-grade tumors and PIN lesions compared to benign tissue. AGR2 transcripts were also detected in urine sediments of patients undergoing prostate biopsy with significantly higher levels in tumor patients. The urine AGR2/PSA transcript ratio allowed much better discrimination between cancer and benign patients than serum total PSA or % free PSA suggesting that urine AGR2 transcripts could be a better marker for the detection of prostate cancer.

In the course of the present invention several new splice variants were cloned and sequenced. The AGR2 transcript variants are shown schematically in FIG. 5. The AGR2 gene comprises 8 exons.

Variants of the AGR2 gene differ from the wild-type AGR2 gene insofar as either complete exons or parts of some exons are deleted. The new splice transcript variants were termed AGR2 SV-C, AGR2 SV-E, AGR2 SV-F, AGR2 SV-G and AGR2 SV-H. The variants are shown schematically in FIG. 5 wherein as wild-type AGR2 the variant B containing shorter part of the untranslated region of the first exon, is designated. In variants C exon 1 is shortened. Variant E comprises exons 1, 5, 7 and 8. Variant F comprises exons 1, 7 and 8. Variant G comprises part of exon 1 and part of exon 7 and exon 8. Variant H comprises exon 2, part of exon 3 and part of exon 8.

BRIEF DESCRIPTION OF THE FIGURES

The present invention is summarized in the Figures and further illustrated in the following examples:

(FIG. 1A) Three populations of vesicles were detected in the blood plasma (left panel). According to the distribution by intensity first population (15% of total amount) consists of EVs with the radius 4.5 nm; second population (43%) consists of EVs with the radius of 23.6 nm which be the size corresponding to exosomes; 41% of total EVs comprise a third population of EVs with the mean radius of about. 254.2 nm and might contain bigger vesicles or agglomerates. The analysis of the distribution of EVs by mass clearly shows that the majority of EVs (95%) is represented by the population of vesicles with the radius of 4.7 nm which might correspond to liposomes. Only a minor part of EVs (4.6%) consists of EVs with the radius of 43 nm, which might correspond to exosomes. Analysis of the distribution by number show that the vesicles with the radius of 4.7 nm represent 99.9%, and the vesicles with the radius of 23.6 nm, which correspond the size of the exosomes, represent 0.09%, and the vesicles with the radius of 254.2 nm comprise about 0.01% of the whole amount.

(FIG. 1B) Vesicles isolated from the urine represented a homogenous population with the average radius of about 74 nm, which as contain EVs with the size, corresponding exosomes, and bigger vesicles as it is shown by electron microscopy (upper panel).

(FIG. 2A) For this analysis 5 patients with prostate adenocarcinoma were chosen. RNA was isolated either from the total blood plasma or from the EVs isolated from the blood plasma.

(FIG. 2B) As a second source of AGR2 and its splice variants, urine sediment and urine EVS were examined. RNA was isolated from these four sources and subjected to the quantitative RT-PCR. GAPDH was used as a reference gene for the normalization of signal intensity. The expression of AGR2 and the splice variants differ between total plasma and plasma vesicles. It is likely that the splice variant AGR2 SV-E might be specifically enriched in the plasma EVs of patients with the prostate cancer. However the analysis of urine EVs delivers more consistent results, supporting application of urine EVs for further analysis.

(FIG. 2C) First, it was verified if the population of urine EVs isolated by differential centrifugation contains exosomes. Urine from the patients 1, 2, and 3 was used for the isolation of proteins from the cell sediment, designated as Se; and from the vesicles, designated as EV. As exosome markers Tsg101, CD9 and Hsp70 were used. GAPDH served as a loading control. Additionally, the presence of prostate specific proteins PSMA was analyzed. In all three patients analyzed PSMA was present on the vesicles isolated from the urine, supporting their origin from the prostate.

(FIG. 3A) AGR2 and all splice variants can serve as potential diagnostic markers allowing to differentiate between benign (BPH) and adenocarcinomas. Additionally, potential predictive value of AGR2 and its splice variants was controlled.

(FIG. 3B) Additionally, The AGR2 svF was demonstrated to show a difference between high and low Gleason scores. Further analysis of a bigger cohort of patients will verify this correlation.

(FIG. 3C) ROC (receiver operator characteristic) plots of the AGR2 variants on the exosomes and PSA on the exosome and protein level in serum (analysis regularly used in the diagnostics) was performed with 27 patients (12 tumor and 9 benign) and revealed significant differences between AGR2 svG and PSA level in serum (p 0.044); AGR2 svG and PSA mRNA in the exosomes (p 0.0195), AGR2svH and PSA in serum (p 0.0269) and AGR2svH and PSA level in the vesicles (0.0274) confirming that the exosome AGR2 can serve as an additional independent diagnostic marker for the prostate cancer allowing to differ between benign disease and prostate cancer with the higher specificity as common markers (e.g. PSA).

To verify if detected mRNAs of AGR2 and its splice variants are indeed enclosed into vesicles, the vesicles from 2 independent samples were treated with RNase. After treatment the RNase was inactivated and the samples were subjected to the RNA isolation followed by the Q RT-PCR. The results showed that the AGR2 and splice variants mRNAs are resistant to the RNase treatment, which support their localization within the EVs.

Figure 5:
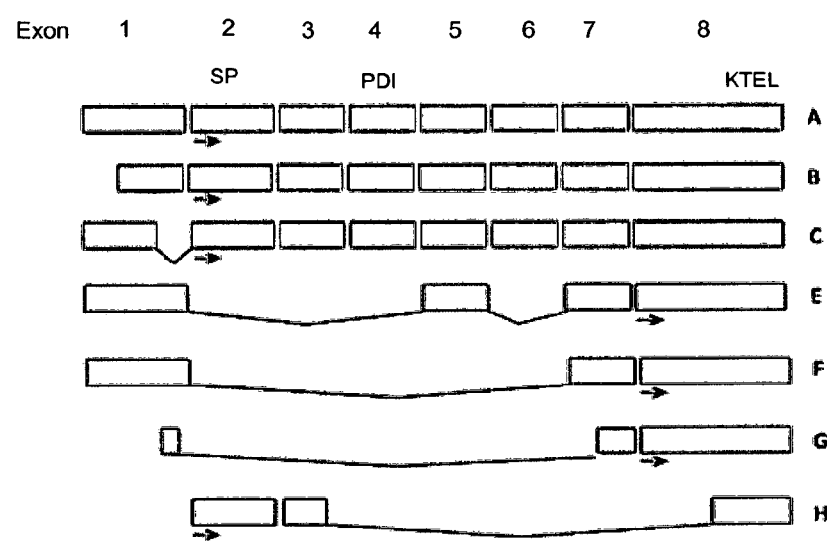

FIG. 5: structural schematic of different splice variants of the AGR2 gene.

The AGR2 gene comprises 8 exons. The exons are shown schematically and the different variants are designated as B-H. A (upper line) corresponds to wild type. It is shown which exon or which part of an exon is deleted in splice variants B to H.

FIG. 6: Comparative analysis of the AGR2 SVs mRNA levels in the breast cancer cells and in exosomes mRNA levels of AGR2 wild type and of splice variants were analyzed in three breast cancer cell lines: MCF7, MDA-MB-361 and MDA-MB-231. The cells were routinely cultured at 37° C. by 95% humidity and 5% CO2. The cellular RNA was isolated using RNeasy Qiagen kit according to the manufacture of the supplier. Exosomes were isolated from the supernatants of the cells grown in serum-free medium for at least 48 hours. Serum-free medium was used to avoid contaminations with the bovine exosomes. Three hundred fifty ml of cell culture supernatant was used from each cell line for the exosome isolation. Exosomes were isolated by differential ultracentrifugation as described elsewhere (Nazarenko et al., 2010 Cancer Research). After sedimentation by ultracentrifugation, exosomes were directly re-suspended in RLT lysis buffer, supplied with the RNeasy Qiagen Kit. Then RNA was isolated according to the manufacture of the supplied. For the production of cDNA, 500 ng of cellular RNA and 30 ng of exosomal RNA were used. Quantitative PCR, using GAPDH and AGR2-specific primers was performed as described above.

Splice variants B, C, G and H were detected in both, cells and exosomes, whereas only splice variant G was strongly enriched on the exosomes. Splice variants A, E and F were detectable only in the cells but not in the exosomes, which differed from the data obtained by the analysis of exosomes derived from the prostate cancer cells. These data suggest a difference in the recruitment of AGR2 splice variants mRNAs to exosomes in different tumor types, which may potentially be used for the diagnosis.

FIG. 7: AGR2 SVs mRNA levels in the exosomes isolated from the urine of 4 patients with urothelial carcinoma.

EVs were isolated from the urine of 4 patients diagnosed with urothelial carcinoma using protocol applied for the isolation of EVs from the urine of the patient with prostate carcinoma. Following differences were observed as compared to the prostate and breast cancer EVs: SV-A is present in EVs isolated from the urine of the patients with urothelial and prostate cancer, but is absent in breast cancer EVs (FIG. 6); The SVs-E, -F, -G shown to be enriched in the EVs of prostate cancer patients, were detectable at low levels only in one out of four patients with urothelial carcinoma.

FIG. 8: AGR2 SVs mRNA levels in the exosomes isolated from the urine of 4 patients with renal cell carcinoma.

EVs were isolated from the urine of 4 patients diagnosed with renal cell carcinoma using protocol applied for the isolation of EVs from the urine of the patient with prostate carcinoma. Following differences were observed as compared to the prostate, breast and urothelial cancer: only SV-A, B, C were detectable in 2 from 4 samples. SV-E, F, G seems to be prostate cancer specific and could not be detected in the EVs derived from the urine of patients with renal cell carcinoma.

FIGS. 9A and 9B: AGR2 SVs mRNA levels in the exosomes isolated from the blood (serum or plasma) of patients with different tumor types.

To assess if blood can be used as a source of EVs for the AGR2-based diagnosis of other different tumor types, blood samples from patients with urothelial and renal cell carcinoma, melanoma, breast and colorectal cancer were used for the isolation of EVS. The GAPDH mRNA was analyzed as a control; additionally, breast cancer cell lines T47D was used as a positive control for the AGR2 wt and splice variants. No AGR2-specific signal could be detected in the EVs isolated from the blood samples of these tumor entities, suggesting that only a very low proportion of EVs, derived from the tumor cells were present in the blood and supporting that urine may be a better source for EV for the diagnosis of prostate, urothelial, renal carcinomas.

DETAILED DESCRIPTION OF THE INVENTION

As shown in the examples below, exosomes isolated from the urine or from the blood of patients can be used as a source for the detection of the biomarkers (ARG2 transcript variants), which allows the application of a non-invasive or only minimally invasive diagnostic routine method. When exosomes are isolated from the urine of patients, the diagnostic method can be performed without any treatment performed by a medical doctor.

Surprisingly, it has been found that distinct ARG2 splice variants recovered from the exosomes can be used as specific diagnostic and/or prognostic markers for different tumor entities. Such tumors comprise not only the preferred prostate tumor but also breast cancer or cancer of colon, lung, pancreas or small intestine to name only a few.

Figure 1A:
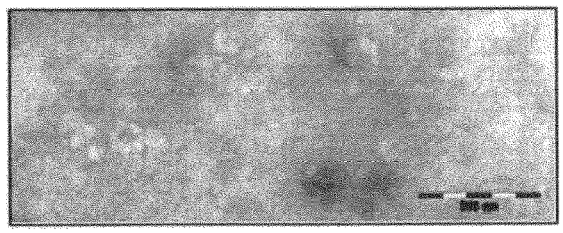
FIGS. 1A and 1B: Characterization of extracellular vesicles (EV) isolated from the plasma and urine of patients with colorectal carcinoma EVs isolated from the blood plasma (A) and urine (B) by differential centrifugation were characterized by transmission electron microscopy (upper panels) and dynamic light scattering analysis (Zetasizer, Malvern Instruments, Germany). To detect different population of vesicles, three main parameter were applied: distribution by intensity (left panel), allowing to visualize vesicles according to the intensity of their fluorescence independent on number; distribution by mass (right panel) according to which the amount of vesicles with certain mass can be measured, and distribution by number (table below), showing the relative amount of vesicles of certain size.
Figure 1A:
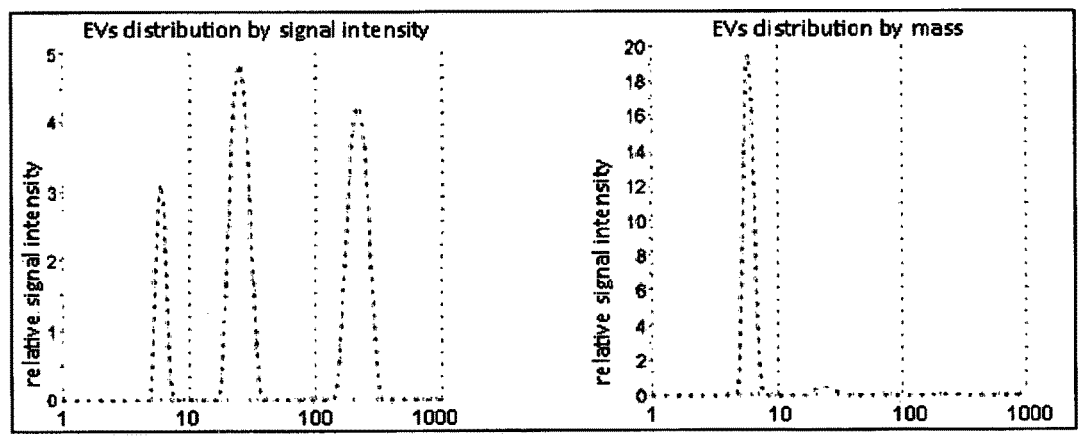
Figure 1B:
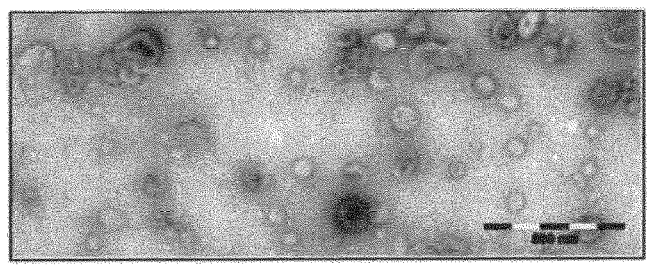
Figure 1B:
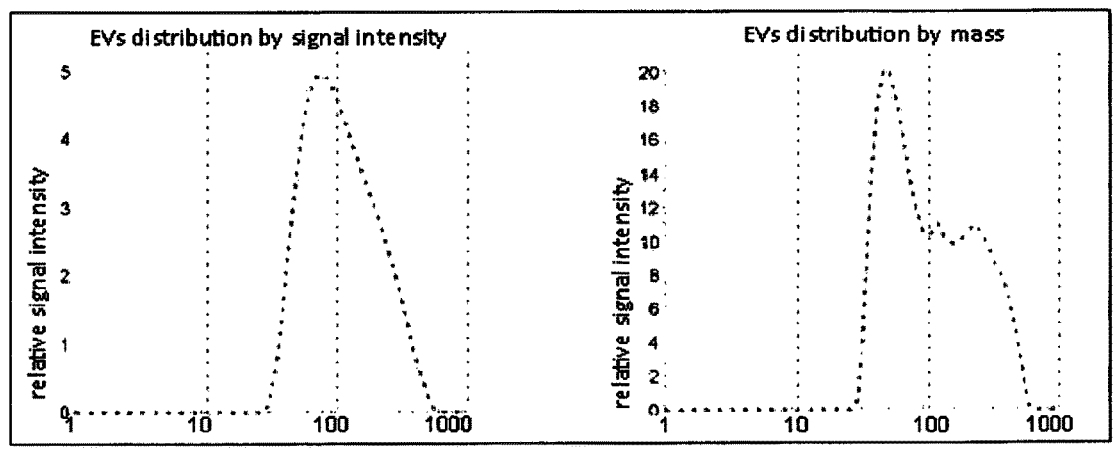
Figure 2A:
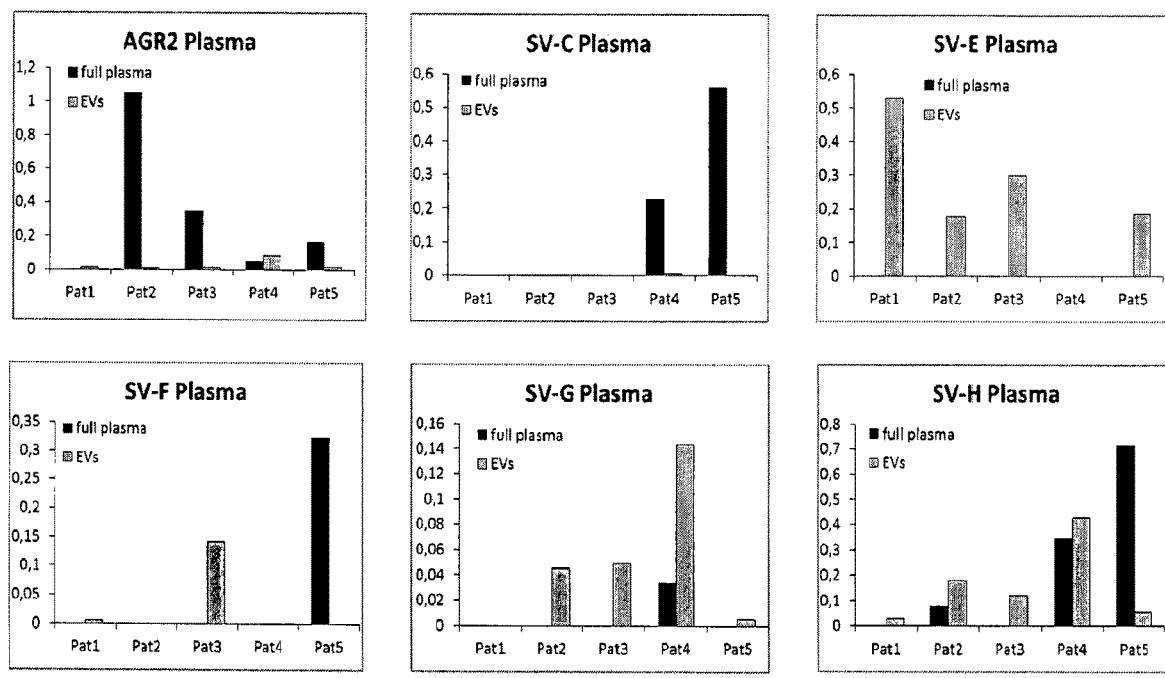
FIGS. 2A-2C: Comparative analysis of the AGR2wt and the splice variants svC, svE, svF, svG, svH mRNA levels in different components of the blood plasma and urine of patients with prostate cancer.

Splice variants E and G (compare with FIG. 5) are enriched in the exosomes isolated from the blood of patients with prostate cancer but not in the cells isolated from the blood. This can be seen from FIG. 2A.

Splice variants E, F, G and H (compare with FIG. 5) are enriched in the exosomes isolated from urine or patients with prostate cancer compared to the urine sediment. This confirms the superior results obtainable by the method of the present invention.

Figure 3A:
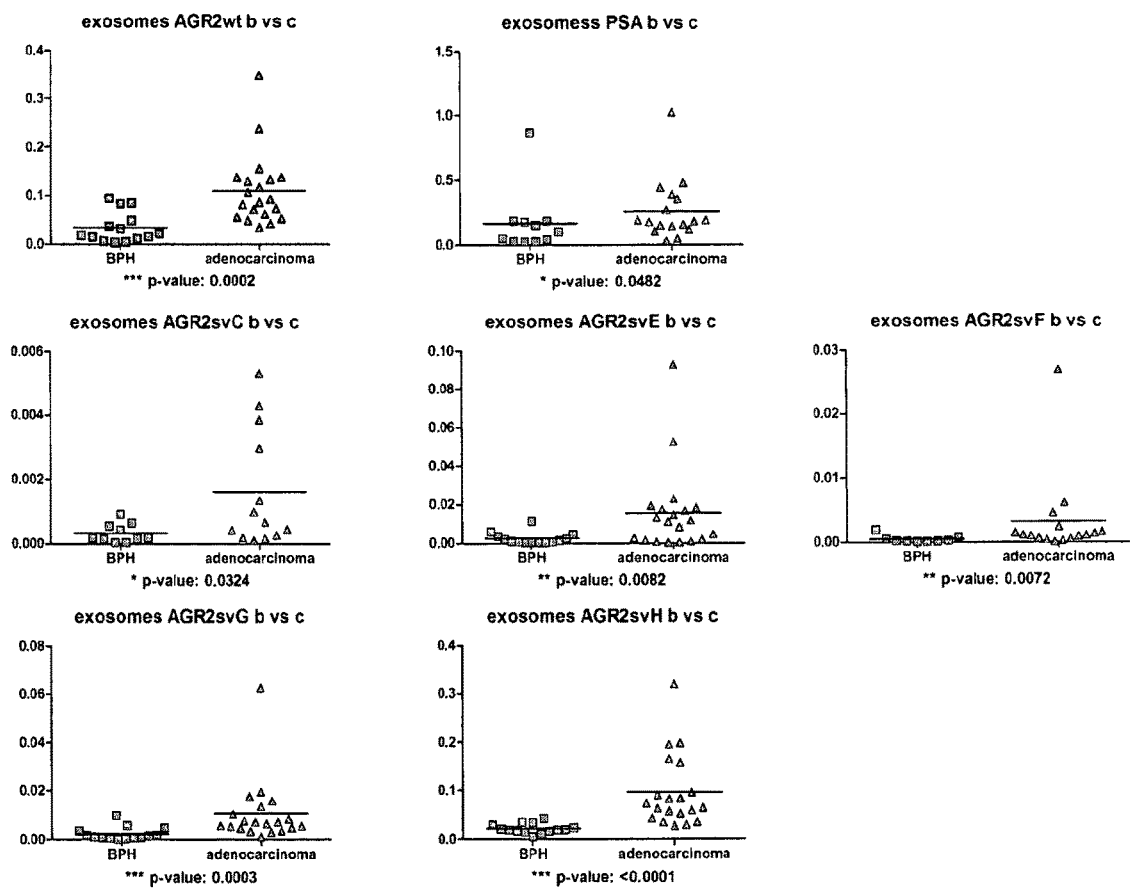
FIGS. 3A-3C: mRNA levels of AGR2 wt and the splice variants in the urine EVs can serve as an independent diagnostic marker for prostate cancer. 39 patients (24 tumors; 15 BPH) with 15 benign and 24 malign adenocarcinoma were included into analysis. EVs were isolated from the urine and were directly used for RNA preparation. 30 ng of RNA were used for the followed quantitative RT-PCR analysis.
Figure 3B:
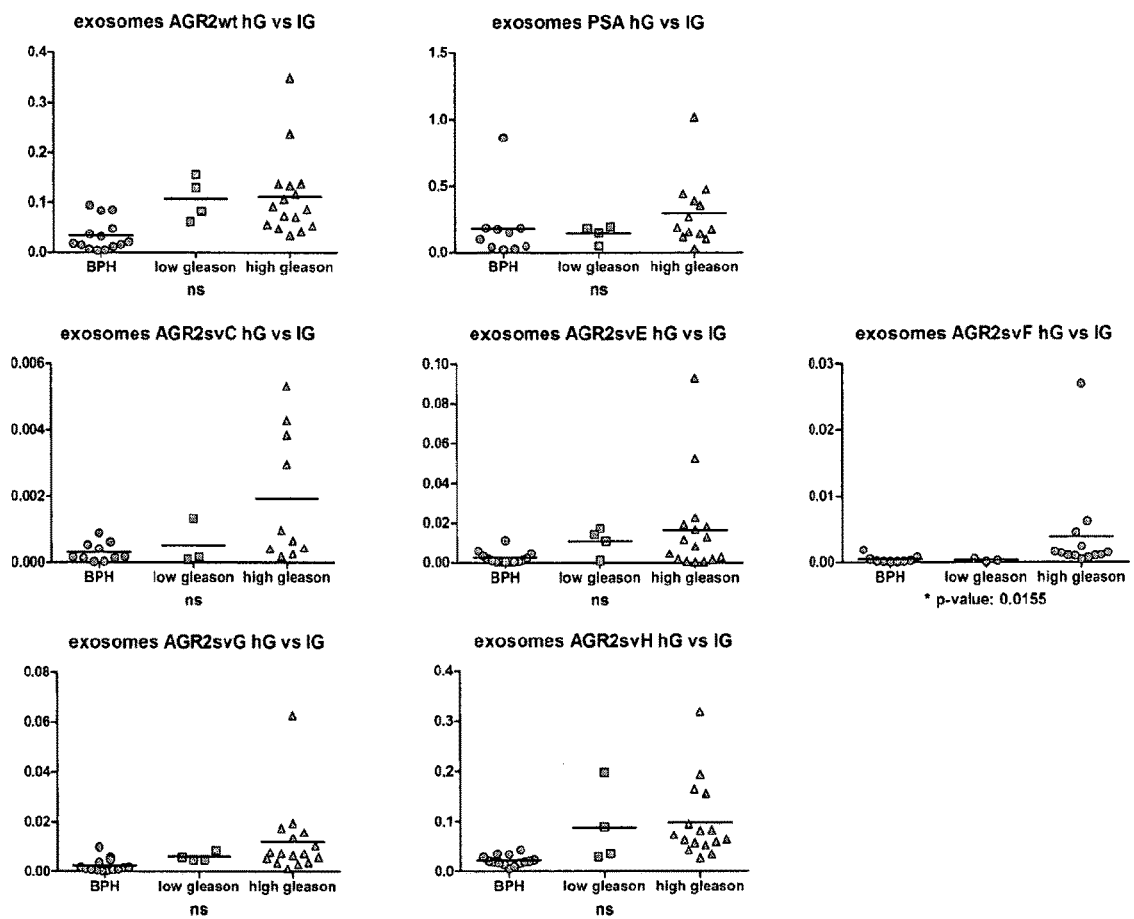
Figure 3C:
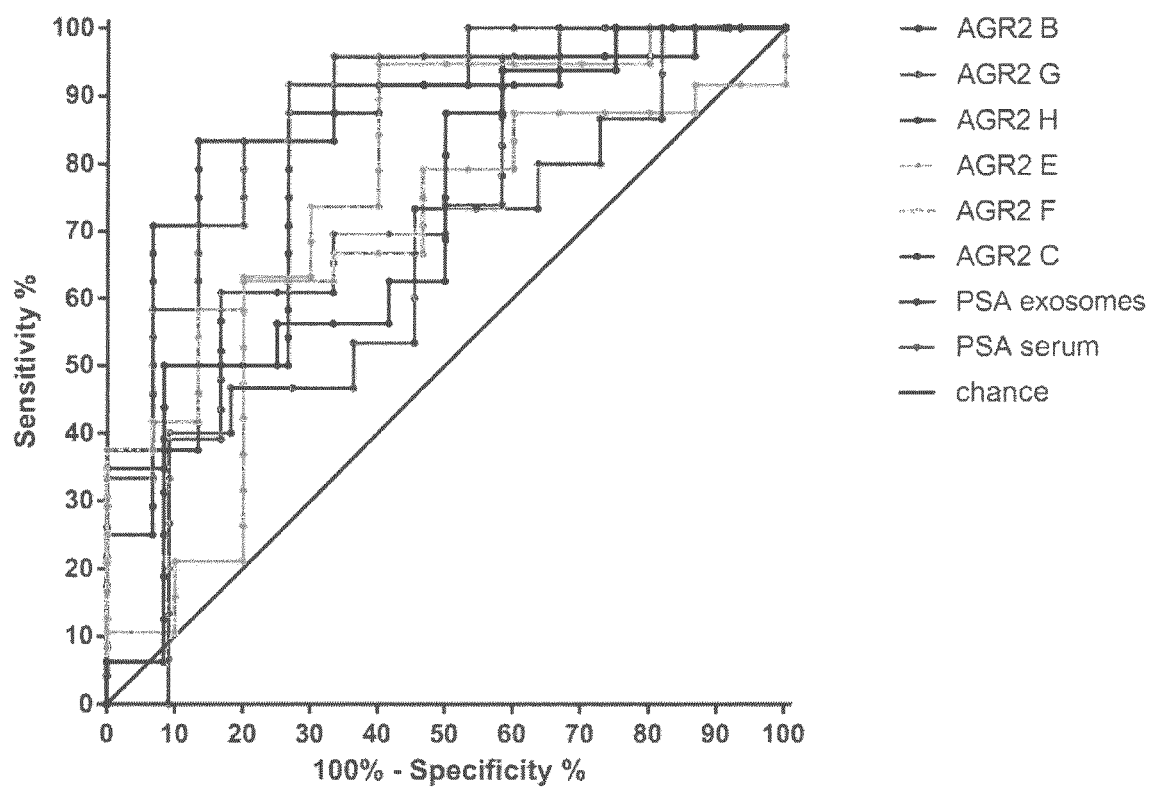
Figure 4:
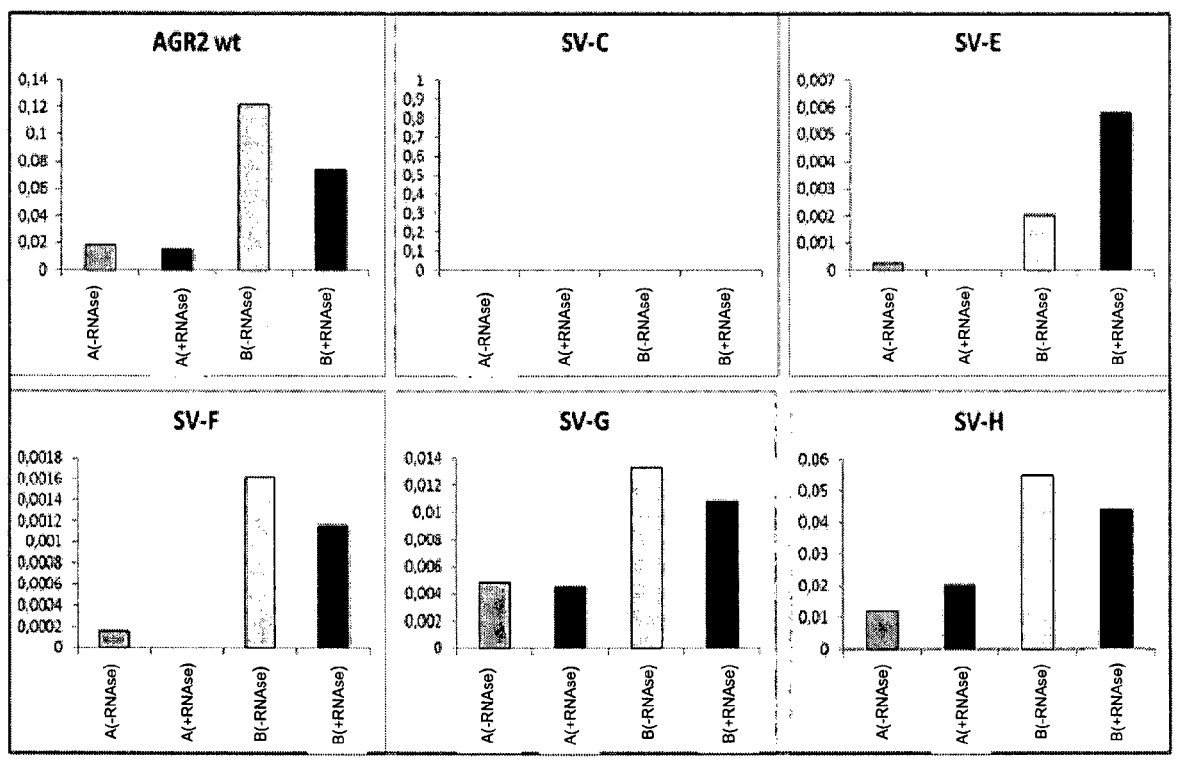
FIG. 4: mRNA of AGR2 wt and the splice variants are most probably enclosed in the EVs and are resistant to the RNase treatment.

A pilot clinical study confirmed that splice variants G and H are enriched in the exosomes isolated from urine of prostate cancer patients and are significantly better diagnostic markers as compared to the serum PSA. This can be seen from FIGS. 3A and 3C of the present application.

In the present invention the following primers were preferred:

```
SV C: Forward:
                                       (SEQ ID NO: 3)
5' CAC AAG GCA GAG TTG CCA TGG 3'

SV E: Forward:
                                       (SEQ ID NO: 4)
5' ATC TGG TCA CCC ATC TCT GA 3'

SV F: Forward:
                                       (SEQ ID NO: 5)
5' GGA AAT CCA GAC CCA TCT CTG 3'

SV G: Forward:
                                       (SEQ ID NO: 6)
5' AAG GCA GGT ACA GCT CTG 3'

Reverse SV C, E, F G:
                                       (SEQ ID NO: 7)
5' TCC ACA CTA GCC AGT CTT CTC A 3'

SV H Forward:
                                       (SEQ ID NO: 8)
5' ATG GAG AAA ATT CCA GTG TCA GCA 3
```

Reverse:
(SEQ ID NO: 9)
5'-ACT TGA GAG CTT TCT TCA TAT GTC TG-3'

AGR2 long transcript: A (was not detected in the exosomes)
AGR2Lt Forward
(SEQ ID NO: 10)
GCCAACAGACAACCCAAAGT AGR2Lt Reverse
(SEQ ID NO: 11)
GCAAGAATGCTGACACTGGA AGR2 short transcript: B (also designated as a wt AGR2)
AGR2St Forward
(SEQ ID NO: 12)
-CGACTCACACAAGGCAGGT- AGR2St Reverse
(SEQ ID NO: 13)
-GCAAGAATGCTGACACTGGA PSA:
PSA Forward
(SEQ ID NO: 14)
ACCAGAGGAGTTCTTGACCCCA PSA Reverse
(SEQ ID NO: 15)
CCCCAGAATCACCCGAGCAG By selection of appropriate forward and reverse primers specific variants could be amplified. The person skilled in the art can, however, easily design alternative primers since the splice variants are described herein and the complete sequence of the gene to be analyzed is known.

Exosomes (extracellular vesicles, EV) are specialized nanovesicles (30-100 nm) that are actively secreted by a variety of normal and tumor cells. Elevated exosome amount has been found in malignancy effusions, serum and urine from cancer patients. Certain RNA transcripts are enriched several 100-fold in the exosomes compared with the donor cells and in particular exosomes are enriched in unique transcripts specific to tumor cells that may be below detection limit even in the tumor cells themselves. Therefore, the mRNA levels of svB, svC, svE, svF, svG and svH (shown in FIG. 5) variant of AGR2 in urine exosomes was analyzed, in order to define the most reliable source of the AGR2 variant as biomarkers for prostate cancer.

The present invention provides an in vitro process for the diagnosis of prostate cancer in exosomes. The term "exosome" is used as a term for "extracellular vesicles". The term "diagnosis" means to obtain more insight in the specific forms of cancer and whether the patient suffers from an aggressive form of prostate cancer or whether possibly other diagnostic markers speak for a benign form which does not require surgery or treatment with strong chemostatic agents. It is an advantage of the present invention that the diagnosis can be performed in a sample obtained from the patient without the action of a doctor. The sample which is used for the diagnostic process is preferably urine. The exosomes can, however, also be obtained from other sources like from bloods serum or plasma. In general the diagnostic method can be performed with fluids obtained from the human body. Body fluids comprise urine, semen, blood (serum of plasma), saliva and any other fluid which can be obtained from the human body.

The diagnostic method of the present invention is performed on exosomes. Therefore, it is essential that the exosomes are enriched and the other components or the fluid containing the exosomes are at least partially removed. Since the detection step is based on the amplification of nucleic acids it is essential that nucleic acids which might interfere with the test results are efficiently removed. Protein components may strongly interfere with the test results when such components inhibit the enrichment of exosomes. Such proteins may for example entrap the exosomes and the nucleic acids contained therein cannot be made accessible to the amplification reaction.

In the following a preferred process for the diagnosis of prostate cancer is described when the body fluid is urine. One of the advantages of using as starting material for diagnosis urine is that the sample can be obtained from the patient without any invasive interaction of a doctor. Moreover, in some cases it may be difficult to obtain a sufficient amount of serum or plasma from a patient. To obtain a sample via biopsy from patients may be even more difficult and may increase the risk to cause metastases by circulating tumor cells or activation of dormant tumor cells.

In the first step of the diagnostic process the exosomes are concentrated from the body fluid, in particular urine of the patient. In a preferred embodiment the urine is first centrifuged at a low speed (preferably up to 4,000 G) at a low temperature (2-15° C.) for 5 to 30 minutes in order to remove remaining cells and debris.

Preferably the supernatant obtained from the first centrifugation step is filtered through suitable filtering means in order to remove remaining large particles from the supernatant. The filter pores preferably have a diameter of about 1 µm to about 150 µm, more preferred about 5 µm to 100 µm.

The urine which has been treated by a low speed centrifugation and possibly an additional filtration step is then preferably ultracentrifuged. In a particularly preferred embodiment the method of the present invention comprises the step of ultracentrifugation. This purification step results in superior test results. The ultracentrifugation can take place either in the presence of a commonly used buffering agent. The ultracentrifugation is usually performed at +4° C. and at G≥100,000 for 20 minutes, preferably from one hour to two hours. As an alternative the samples can be purified by chromatography- or precipitation-based approaches. It is important to enrich the extracellular vesicles with suitable purification steps from the body fluids.

The sediment obtained in the ultracentrifugation step is then further treated to extract the RNA from the exosomes. It is preferred to treat the sediment with proteases and DNAses or other suitable chemicals in order to extract the RNA from the sediment as efficiently as possible.

For the analysis of the RNA fractions obtained from this step the RNA is first transcribed into cDNA with the help of a reverse transcription.

The cDNA obtained in this manner is amplified with a polymerase chain reaction whereby specific primers developed in the course of the present invention are preferably used. From the nucleotide sequence of AGR2 (SEQ ID NO:1) and the complement thereof suitable parts are selected. Then it has to be checked whether said primers do potentially amplify other sequences which may result in false-positive reactions. In the course of the present invention the following primers are especially preferred: SEQ ID NO:3 to SEQ ID NO:13 which allow the amplification of variants of distinct splice variants of AGR2. To avoid artifacts, for a PCR reaction usage of 2 different primer pairs or preferably 3 primer pairs is more preferred.

After having performed the PCR reaction the amplification products are analyzed. It is well-known in the art, how such analysis can be performed. In a preferred embodiment the nucleic acid is amplified in a quantitative PCR.

Depending on the results the diagnosis can be performed. The presence or absence of specific variants of the AGR2 gene allows a diagnosis whether the patient suffers from a malignant prostatic cancer or whether the clinical symptoms are benign.

The experimental results show that mRNAs coding for isoforms B, E, G and H are significantly elevated in tumor patients compared with samples obtained from patients with benign forms according to the student-t test. The isoforms G and H demonstrated significantly higher specificity and sensitivity compared to the currently applied standard PSA test. Therefore, it is preferred to detect the presence and/or absence of the isoforms G, H, B and E either alone or in combination.

Since the diagnostic process of the present invention is also based on the observation whether certain variants are overly expressed or expressed only to a very low level it is preferred to standardize the test method. This can be done for example by using always the same concentration of RNA in the test. It is preferred to standardize the RNA level to 10-50 ng, preferably to 30 ng per sample to be amplified.

Another alternative to improve the reliability of the diagnostic result is to amplify together with the AGR2 variants also a housekeeping gene. A so-called "housekeeping gene" may serve as internal standard which allows a comparison of results obtained in different experiments. Such as housekeeping gene is preferably the gene GAPDH which is present in all samples. Of course other housekeeping genes, recruited to the exosomes can also be used. In case PSA is amplified, suitable primers are SEQ ID NO:14 and SEQ ID NO:15.

It is one object of the present invention to determine whether splice variants of the AGR2 gene can be amplified and thereafter be assigned to certain types of diseases, in particular different tumors, and furthermore whether nucleic acid coding for certain splice variants can be detected in exosomes obtained from the urine of patients.

AGR2 has also been shown to be expressed in several human tissues rich in epithelial cells, like prostate, breast, small intestine, colon, lung, and pancreas. Its protein level was found increased in prostate tumor tissue and its expression level was associated with poor survival of prostate cancer patients. Therefore, the method of the present invention may serve as means for a prediction of the further development of the disease and as means for differentiating one type of tumor from another.

In breast and prostate adenocarcinoma, AGR2 seems to be under the control of ER or androgen receptor expression. Up-regulation of AGR2 enhances classical hallmarks of cancer, such as metastasis, invasion, colony formation, and proliferation.

The present invention is further illustrated in the following examples whereby the results are shown in the enclosed figures. Important aspects of the present invention can be summarized as follows:

Splice variants E and G are enriched in exosomes isolated from the blood of patients suffering from prostate cancer. Such splice variants were, however, not detected in cells isolated from blood (compare with FIG. 2A).

Figure 2B:
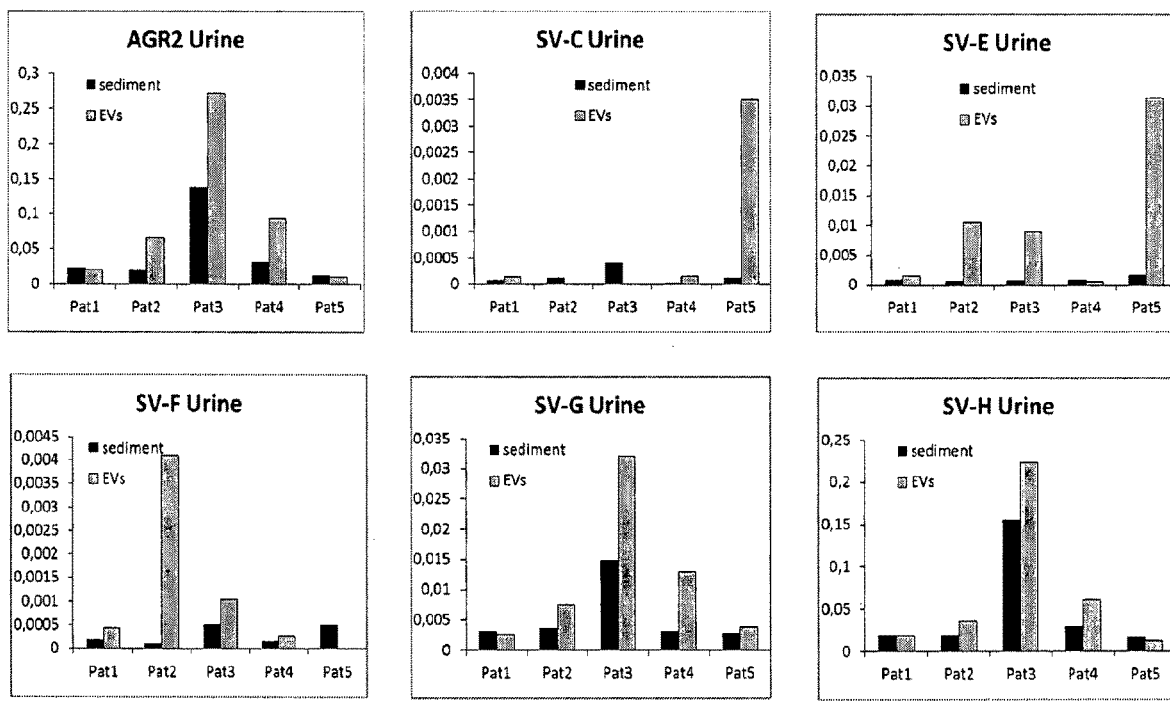
Figure 2C:
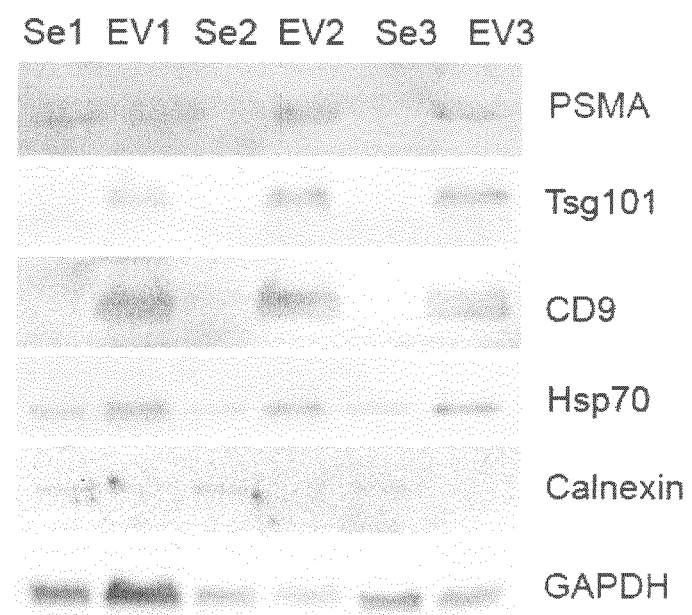

Splice variants E, F, G and H are enriched in exosomes isolated from urine of patients suffering from prostate cancer as compared to the urine sediment. The result that the exosomes allow superior diagnostic results could not have been expected. This can be seen from FIG. 2B.

Clinical pilot studies confirmed that splice variants G and H are enriched in the exosomes isolated from urine of patients suffering from prostate cancer patients. Those splice variants are significantly better diagnostic markers as compared to serum PSA. This can be seen from FIG. 3A or 3C, respectively.

The analysis of ARG2 splice variants from the exosomes obtained from blood and/or urine is tumor type specific. FIG. 6 for example shows the enrichment of AGR2 splice variants in breast cancer exosomes which may allow the distinction between breast and prostate cancer.

Splice variant C is present in breast cancer exosomes but absent in prostate cancer whereas variant A is present in the exosomes derived from patients suffering from prostate cancer but absent in exosomes obtained from patients suffering from breast cancer. Even if prostate cancer and breast cancer are highly specific to gender such distinction may also be useful in the molecular diagnostic of other cancer types.

The present invention is summarized in the Figures above and further illustrated in the following examples:

Example 1: Clinical Samples

The use of clinical samples for the study was approved by the ethics committee of the Innsbruck Medical University. Frozen prostate tissue samples from previously untreated patients who had undergone radical prostatectomy after tumor diagnosis in a PSA-based prostate cancer early detection program were obtained from the prostate center of the Department of Urology of the Innsbruck Medical University. Frozen tissue samples were processed and microdissected and RNA was isolated. Tumor samples were obtained from a cohort of Gleason score (GSC) 8 tumors (Gleason pattern 3) and a group of GSC 8-10 tumors (Gleason patterns 4 and 5). Benign epithelial cell samples were isolated from the same specimens apart from tumor loci.

Example 2: Patients with Clinical Diagnosis

This example included 30 patients, with prostate cancer and with benign prostate hyperplasia. Analysed were in each case a urine sample and a blood sample (serum).

The cancer cases were all detected by biopsy. Before prostatic specific antigen (PSA) was measured and patients with a high PSA-level were advised to undergo a transrectal guided biopsy. Their age was in between 28 and 78. As regards the histologic classification only patients with a gleason score from 6 to 9 were chosen.

All patients with prostate cancer were treated by radical prostatectomy and pelvic lymphadenectomy.

The patients with benign prostate hyperplasia with a low PSA-level (<4 ng/ml) were treated by transurethral resection. If the PSA-level of these patients was high prostate cancer was obviated by transrectal guided biopsy following by transurethral resection.

Example 3: Splice Variants of AGR2

AGR2 has a fairly broad expression pattern in human tissues. However splice variants of AGR2 (e.g. the long form, Δ6 and Δ4-6) are reported to provide some selectivity by being predominantly expressed in certain tissues or in distinct hepatocellular neoplasms. It was therefore investigated whether further splice variants of AGR2 exist and whether they would be a better predictor of prostate cancer development.

In PCR amplification reactions which were carried out with primers in exon I and 8, and 6 new splice transcripts were identified which were termed sv C, E, F, G,H in addition to transcripts A and B that have already been reported as long and short transcripts of AGR2 (compare with FIG. 5). The transcripts C-H most likely arose from alternative splicing as they lack partial or complete exons. In contrasts to transcripts A and B that are known to encode the full length AGR2 protein, no protein products for transcripts C, E, F, G and H have been detected so far.

Example 4

As a further characterization of the splice variants, their expression pattern was examined in different cells lines to find out whether they would differentiate between cells of prostate from cells of non-prostate origin. For prostate cells, VCaP, LNCaP, PNT2 and 22Rv.1 cell lines were used whereas the non-prostate cells which were analyzed consisted of breast tumor (T47D, MCF7), endometrial tumor (Ishikawa), cervical tumor (HeLa), kidney tumor (Hek 293), liver tumor (HepG2) and choriocarcinoma cells (JEG-3). AGR2 (short form transcript; svB) was expressed in several cell lines in agreement with reports on its widespread expression. In contrast, it was found that the AGR2 long isoform (sv A) which was previously reported to be expressed in predominantly prostate tissue, was not only expressed in the prostate tumor cell lines but also in mammary (MCF7 and T47D) and endometrial cell lines (Ishikawa). The sv C, E, F, G and H showed varying levels of expression among the different cell lines with sv C being mainly expressed in prostate tumor cell lines. This differential expression pattern of the splice variants and their levels can be used to differentiate in the progression of prostate cancer from the benign to the more advanced stages of the tumor.

Example 5: AGR2 Splice Variants in Prostate Cancer Progression

A real-time qPCR was performed for the different AGR2 transcripts on prostate biopsies which consisted of 32 benign biopsies and 32 tumor samples (16 from Gleason pattern 3 and 16 from Gleason pattern 4). In the quantitative RT-PCR the splice variant sv B (short transcript) again showed a significant difference (p=0.0406) between benign and prostate tumor. In addition sv H was also identified as a predictive discriminator of benign and prostate tumor (p=0.0476). All the other splice variants did not show any significant difference in the two sample pools. Since non-invasive diagnostics (using urine or saliva samples) are superior alternatives to traditional needle or excision biopsies due to the reduced patient pain and inconvenience, and greater speed and lower cost of analysis, it was decided to examine the expression of the splice variants in urine sediments.

Example 6: Urine Exosomes for Studying AGR2 Expression

AGR2 (svB) splice variant is present in urine sediments of patients with prostate cancer and their levels correlate with the tumor aggressiveness allowing discrimination between benign and malignant neoplasm outperforming markers currently used for the diagnostic of prostate cancer. It was tested whether newly identified splice variants are also present in urine sediments and these studies were extended to determine whether they are also present in urine exosomes.

Urine extracellular membrane vesicles were isolated by differential centrifugation and characterized by dynamic light scattering. This showed that the urine exosomes are of sizes 74.0±85.9 nm. The expression of the AGR2 splice variants in urine sediments and urine exosomes in 5 patients diagnosed with prostate carcinoma was compared to find out whether the spliced variants are indeed enriched in exosomes. In all 5 samples, the level of expression of the splice variants was higher in the urine exosomes than in the sediments suggesting that these transcripts are enriched in the exosomes and are most likely a more appropriate source for AGR2 as a non-invasive diagnostic marker.

As exosomes are somewhat unique in their protein composition, the level of a few markers was analyzed as additional traits for the identity of the exosomes in the urine sediments and exosome preparation of 3 of the isolated samples. It could be shown that TSG191, CD9, Hsp70 are all overexpressed in the exosome preparation compared to the urine sediments of the 3 samples. Furthermore we could show that PSMA is enriched in the exosomal vesicle fraction indicating the prostate origin of these samples.

For that purpose AGR2 wt and sv mRNA levels were examined in urine sediments and in exosomes isolated from 5 patients diagnosed with prostate carcinoma. The urine extracellular membrane vesicles were isolated by differential centrifugation and characterized by dynamic light scattering using Zetasizer instrument (Malvern Instruments GmbH).

Example 7: The AGR2 wt and Splice Variants mRNA is Enriched in the Urine Exosomes The previous work showed that AGR2 wt mRNA and the transcripts of splice variants (sv) were present in urine sediments of patients with prostate cancer. Statistical analysis revealed that the AGR2 mRNA levels correlate with the tumor aggressiveness and allows discriminating between malign and benign tumors, outperforming markers currently used for the diagnostic of prostate cancer. Based on these findings the mRNA levels of AGR2 wt and svC, svE, svF, svG, svH were compared in different physiological fluids and tested if these mRNA is available as a circulation cell-free component or as an entire part of the extracellular membrane vesicles, e.g. exosomes, in order to define the most reliable source of the AGR2wt or sv mRNA as biomarkers for prostate cancer.

For that purpose AGR2 wt and sv mRNA levels were examined in blood plasma and in the extracellular membrane vesicles isolated form the plasma in 4 patients diagnosed with prostate carcinoma. Exosome-depleted plasma did not contain detectable levels of RNA and therefore was not included into analysis. Additionally, urine sediments and urine exosomes from the same patients were examined. Prostate specific gene PSA and GAPDH mRNA were analyzed as controls.

The plasma and urine extracellular membrane vesicles were isolated by differential centrifugation and characterized by dynamic light scattering using Zetasizer instrument (Malvern Instruments GmbH).

The analysis shows three distinct vesicles population in the blood: population1 with radius 4.7 nm, population 2 with radius 23.6 nm, which might correspond exosomes, and the population 3 with radius 254.2 nm, which might contain either bigger vesicles or the agglomerates of vesicles.

Example 8: AGR2 Splice Variants Obtained from Exosomes are Tumor Type Specific

By using the methods as described in the previous examples the presence or absence of ARG2 splice variants was analyzed in samples obtained from patients suffering from other tumor types or in the exosomes derived from cancer cells lines. The results are shown in FIGS. 6-8B.

In the experiments leading to the results shown in FIG. 6, ARG2 splice variants were analyzed in breast cancer cell lines and in the exosomes derived from these cell lines.

The experiments leading to the results shown in FIG. 6 allow to speculate that the recruitment of AGR2 splice variants is tumor type-specific and will for instance allow a discrimination between breast cancer and prostate cancer. Splice variant C is present in breast cancer exosome but absent in prostate cancer. On the other side splice variant A is present in the exosomes derived from a patient suffering from prostate cancer but absent in samples obtained from breast cancer cells. Consequently the combinational application of translated and non-translated AGR2 splice variants offers a unique possibility for the diagnosis and prognosis of different tumor entities.

The invention claimed is:

1. An in vitro process for the diagnosis of prostate cancer using exosomes obtained from a body fluid of a patient, said process comprising the steps of:
 a) concentrating exosomes from the body fluid of the patient, wherein the body fluid is urine,
 b) extracting the total RNA from the exosomes obtained in step a),
 c) converting the RNA obtained in step b) to cDNA,
 d) amplifying the cDNA obtained in step c) with a polymerase chain reaction (PCR) using primers derived from the anterior gradient 2 (AGR2) nucleotide sequence or the complement thereof, and
 e) detecting and measuring splice variants of the AGR2 gene selected from the group consisting of AGR2 SV-C, AGR2 SV-E, AGR2 SV-F, AGR2 SV-G and AGR2 SV-H.

2. The process according to claim 1, wherein the step of concentrating said exosomes according to step a) is performed via ultracentrifugation of the body fluid in a buffer at G-force ≥100,000 for at least 30 minutes.

3. The process according to claim 1, wherein the step of concentrating said exosomes according to step a) includes the steps of:
 a1) centrifuging the body fluid at low speed in order to remove cells and debris,
 a2) filtering the supernatant through a filtering means,
 a3) ultracentrifuging the supernatant, and
 a4) harvesting a fraction containing the exosomes.

4. The process according to claim 1, wherein the RNA is extracted from the exosomes in step b) by treatment with DNAse and at least one protease.

5. The process according to claim 1, further comprising the additional step of determining the concentration of RNA in the sample and adjusting said concentration to between 10 to 50 ng RNA.

6. The process according to claim 1, wherein the RNA is converted to cDNA in step c) by reverse transcription.

7. The process according to claim 1, whereby step d) further includes the step of amplifying a housekeeping gene.

8. The process according to claim 7 wherein the housekeeping gene is glyceraldehyde 3-phosphate dehydrogenase (GapDH) and/or prostatic specific antigen (PSA).

9. The process according to claim 1, wherein the primers utilized in step d) comprise a forward and reverse primer pair selected from the group consisting of SEQ ID NO:3 and SEQ ID NO:7, SEQ ID NO: 4 and SEQ ID NO:7, SEQ ID NO:5 and SEQ ID NO:7, SEQ ID NO:6 and SEQ ID NO:7, and SEQ ID NO:8 and SEQ ID NO:9.

10. The process according to claim 1, wherein the PCR is a quantitative PCR.

11. The process according to claim 1, wherein the exosomes obtained in step a) are further purified from the body fluid by a chromatography step.

12. The process according to claim 1, wherein the exosomes obtained in step a) are further purified from the body fluid by a precipitation step.

13. The process according to claim 1, further comprising the additional step of determining the concentration of RNA in the sample and adjusting said concentration to 30 ng RNA.

\* \* \* \* \*